US00PP24158P2

(12) United States Plant Patent
Kobayashi

(10) Patent No.: US PP24,158 P2
(45) Date of Patent: Jan. 14, 2014

(54) POINSETTIA PLANT NAMED 'PERHC59B'

(50) Latin Name: ***Euphorbia*×hybrid**
Varietal Denomination: PERHC59B

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 113 days.

(21) Appl. No.: 13/385,062

(22) Filed: Jan. 31, 2012

(51) Int. Cl.
*A01H 5/00* (2006.01)

(52) U.S. Cl.
USPC ..... Plt./307; Plt./302; Plt./303

(58) Field of Classification Search
USPC ..... Plt./302, 303, 307
See application file for complete search history.

*Primary Examiner* — Susan McCormick Ewoldt
(74) *Attorney, Agent, or Firm* — C. A. Whealy

(57) ABSTRACT

A new and distinct cultivar of *Euphorbia* plant named 'PERHC59B', characterized by its uniform, upright and mounded plant habit; vigorous growth habit; freely branching habit; dark green-colored leaves; early season flowering response; large inflorescences with bright red purple-colored flower bracts with light pink-colored margins; and good post-production longevity.

1 Drawing Sheet

Botanical designation: *Euphorbia*×hybrid.
Cultivar denomination: 'PERHC59B'.

BACKGROUND OF THE INVENTION

The present invention relates to a new and distinct cultivar of *Euphorbia* plant, botanically known as *Euphorbia*×hybrid, and hereinafter referred to by the name 'PERHC59B'.

The new *Euphorbia* plant is a product of a planned breeding program conducted by the Inventor in Encinitas, Calif. The objective of the breeding program is to create new uniform *Euphorbia* plants having large inflorescences with bright red purple-colored flower bracts and excellent post-production longevity.

The new *Euphorbia* plant originated from a cross-pollination made by the Inventor in May, 2006 of a proprietary selection of *Euphorbia*×hybrid identified as code number PE3-63, not patented, as the female, or seed, parent, with a proprietary selection of *Euphorbia*×hybrid identified as code number 76-01, not patented, as the male, or pollen, parent. The new *Euphorbia* plant was discovered and selected by the Inventor as a single flowering plant within the progeny of the stated cross-pollination in a controlled greenhouse environment in Encinitas, Calif. in December, 2007.

Asexual reproduction of the new *Euphorbia* plant by terminal vegetative cuttings in a controlled greenhouse environment in Encinitas, Calif. since January, 2008 has shown that the unique features of this new *Euphorbia* plant are stable and reproduced true to type in successive generations of asexual reproduction.

SUMMARY OF THE INVENTION

Plants of the new *Euphorbia* have not been observed under all possible environmental conditions and cultural practices. The phenotype may vary somewhat with variations in environment such as temperature, daylength and light intensity, without, however, any variance in genotype.

The following traits have been repeatedly observed and are determined to be the unique characteristics of 'PERHC59B'.

These characteristics in combination distinguish 'PERHC59B' as a new and distinct *Euphorbia* plant:

1. Uniform, upright and mounded plant habit.
2. Vigorous growth habit.
3. Freely branching habit.
4. Dark green-colored leaves.
5. Early season flowering response; under natural season conditions, plants flower in early November in Southern California.
6. Large inflorescences with bright red purple-colored flower bracts with light pink-colored margins.
7. Good post-production longevity.

In side-by-side comparisons conducted in Encinitas, Calif., plants of the new *Euphorbia* differ primarily from plants of the female parent in the following characteristics:

1. Plants of the new *Euphorbia* are more freely branching than plants of the female parent selection.
2. Plants of the new *Euphorbia* have darker green-colored leaves than plants of the female parent selection.
3. Flower bracts of plants of the new *Euphorbia* are bright red purple in color whereas flower bracts of plants of the female parent selection are bright red in color.

In side-by-side comparisons conducted in Encinitas, Calif., plants of the new *Euphorbia* differ primarily from plants of the male parent selection in flower bract color as flower bracts of plants of the new *Euphorbia* are bright red purple in color whereas flower bracts of plants of the male parent selection are medium pink in color.

Plants of the new *Euphorbia* can be compared to plants of the *Euphorbia*×hybrid 'PERHC18B', not patented. In side-by-side comparisons conducted in Encinitas, Calif., plants of the new *Euphorbia* differed primarily from plants of 'PERHC18B' in the following characteristics:

1. Plants of the new *Euphorbia* were more vigorous than plants of 'PERHC18B'.
2. Flower bracts of plants of the new *Euphorbia* were bright red purple in color whereas flower bracts of plants of 'PERHC18B' were medium pink in color.

Plants of the new *Euphorbia* can also be compared to plants of the *Euphorbia pulcherrima*×*Euphorbia cornastra* 'Eckcory', disclosed in U.S. Plant Pat. No. 15,849. In side-by-side comparisons conducted in Encinitas, Calif., plants of the new *Euphorbia* differed primarily from plants of 'Eckcory' in the following characteristics:

1. Plants of the new *Euphorbia* had thicker lateral branches than plants of 'Eckcory'.
2. Flower bracts of plants of the new *Euphorbia* were bright red purple in color whereas flower bracts of plants of 'Eckcory' were hot pink in color.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the bottom of the sheet comprises a side perspective view of a typical flowering plant of 'PERHC59B' grown in a container.

The photograph at the top of the sheet is a close-up view of a typical inflorescence of 'PERHC59B'.

DETAILED BOTANICAL DESCRIPTION

Plants used in the aforementioned photographs and in the following description were grown during the autumn and winter in 16.5-cm containers in a polyethylene-covered greenhouse in Encinitas, Calif. and under natural season conditions and cultural practices which approximate those generally used in commercial *Euphorbia* production. During the production of the plants, day temperatures averaged 24° C., night averaged 17° C. and light levels ranged from 3,500 to 4,500 foot-candles. Measurements and numerical values represent averages for typical flowering plants. Plants were pinched one time and were 18 weeks old when the photographs and the description were taken. In the following description, color references are made to The Royal Horticultural Society Colour Chart, 2007 Edition, except where general terms of ordinary dictionary significance are used.

Botanical classification: *Euphorbia*×hybrid 'PERHC59B'.

Parentage:

*Female, or seed, parent.*—Proprietary selection of *Euphorbia*×hybrid identified as code number PE3-63, not patented.

*Male, or pollen, parent.*—Proprietary selection of *Euphorbia*×hybrid identified as code number 76-01, not patented.

Propagation:

*Type.*—Terminal vegetative cuttings.

*Time to initiate roots.*—About one to two weeks at 20° C. night temperature and 27° C. day temperature.

*Time to produce a rooted young plant.*—About four weeks at 20° C. night temperature and 27° C. day temperature.

*Root description.*—Fibrous; white in color.

Plant description:

*Plant habit and form.*—Uniform, upright and mounded plant habit; inverted triangle; large inflorescences positioned above the foliar plane; vigorous growth habit.

*Plant height.*—About 42 cm.

*Plant diameter or spread.*—About 52 cm.

*Lateral branch description.*—Quantity: Freely branching habit, about seven lateral branches develop after pinching. Length: About 35 cm. Diameter: About 7 mm. Internode length: About 3.2 cm. Strength: Strong. Texture: Smooth, glabrous. Color: Close to 146A.

*Foliage description.*—Arrangement: Alternate, simple. Aspect: Flat. Length: About 11.5 cm. Width: About 6.5 cm. Shape: Lanceolate to elliptical. Apex: Acute. Base: Rounded attenuate. Margin: Entire. Venation pattern: Pinnate, arcuate. Texture, upper surface: Sparsely pubescent. Texture, lower surface: Pubescent. Color: Developing leaves, upper surface: Close to 139A. Developing leaves, lower surface: Close to N137D. Fully expanded leaves, upper surface: Close to N189A; venation, close to 138B. Fully expanded leaves, lower surface: Close to N137D; venation, close to 147C. Petiole: Length: About 6.2 cm. Diameter: About 2 mm. Texture, upper and lower surfaces: Sparsely pubescent. Color, upper and lower surfaces: Close to 146B.

Inflorescence description:

*Inflorescence type and habit.*—Inflorescences are compound corymbs of cyathia with colored flower bracts subtending the cyathia; inflorescences positioned above the foliar plane.

*Quantity of inflorescence.*—One inflorescence develops per lateral branch.

*Fragrance.*—None detected.

*Flowering response.*—Early season flowering response; under natural season conditions, plants typically flower in early November in Southern California; under artificial long nyctoperiod/short photoperiod conditions, plants flower about 8.5 weeks later.

*Post-production longevity.*—Good post-production longevity; plants of the new *Euphorbia* maintain good substance and flower bract color for about four weeks under interior conditions; inflorescences persistent.

*Inflorescence size.*—Diameter: About 26 cm by 27.5 cm. Height (depth): About 6.5 cm.

*Flower bracts.*—Quantity per inflorescence: About 16. Length, largest bracts: About 9.5 cm. Width, largest bracts: About 4.8 cm. Shape: Elliptical. Apex: Acute to slightly acuminate. Base: Equilateral to slightly attenuate. Margin: Entire. Texture, upper and lower surfaces: Smooth, glabrous. Aspect: Initially angling upwardly and becoming closer to horizontal with development. Venation pattern: Pinnate, arcuate. Color: Developing or transitional bracts, upper surface: Close to N57D; irregular splotches, close to 11D; towards the margins, close to 143B to 143C. Developing or transitional bracts, lower surface: Close to 11D; towards the apex and margins, close to 138B to 138C. Fully expanded bracts, upper surface: Close to N57A; at the margins, close to 56D; color becoming closer to N57B to N57C with development. Fully expanded bracts, lower surface: Close to 11D overlain with close to N57D and 68C; color becoming closer to 11D tinted with close to 69A. Bract petiole: Length: About 2.5 cm. Diameter: About 1.5 mm. Texture, upper and lower surfaces: Smooth, glabrous. Color, upper and lower surfaces: Close to 144B.

*Cyathia.*—Quantity per corymb: About 45. Length: About 3 mm. Width: About 2.5 mm. Shape: Round. Color, immature: Close to N144A. Color, mature: Close to 146D.

*Nectaries.*—None observed.

*Peduncles.*—Length: About 1 mm. Diameter: About 1 mm. Strength: Strong. Aspect: Upright to outwardly. Texture: Smooth, glabrous. Color: Close to 146C.

*Reproductive organs.*—Stamens: Plants of the new *Euphorbia* have not been observed to develop stamens. Pistils: Plants of the new *Euphorbia* have not been observed to develop pistils.

*Seeds and fruits.*—Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 15° C. to about 30° C.

It is claimed:

1. A new and distinct *Euphorbia* plant named 'PERHC59B' as illustrated and described.

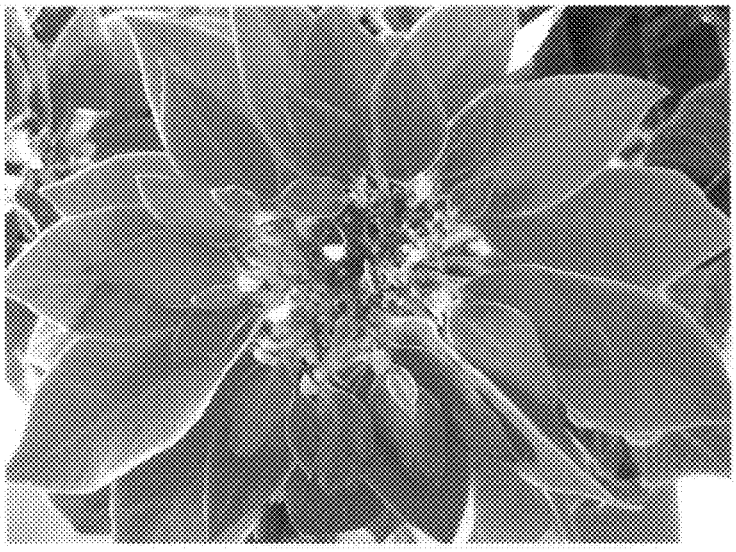
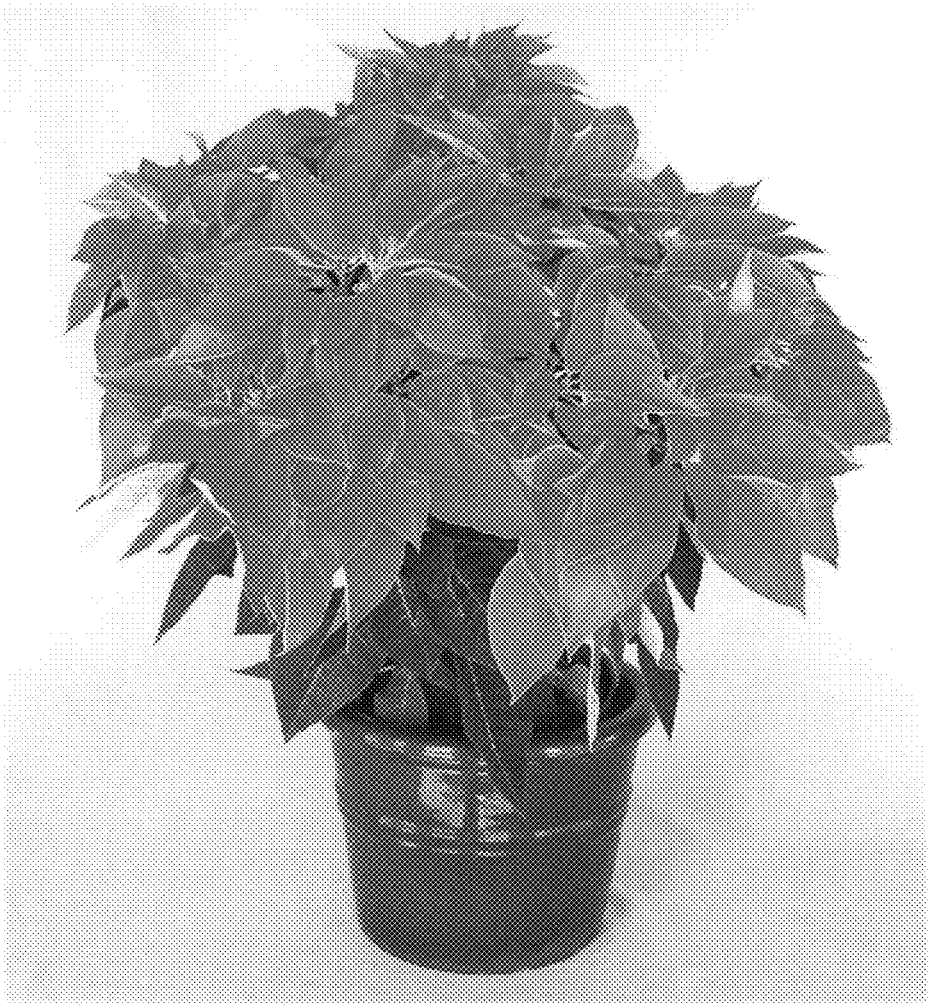

* * * * *